United States Patent
Van Kesteren et al.

(10) Patent No.: US 9,636,058 B2
(45) Date of Patent: May 2, 2017

(54) SENSOR FOR DETERMINING CONCENTRATION OF GAS

(71) Applicant: KONINKLIJKE PHILIPS N.V., Eindhoven (NL)

(72) Inventors: Hans Willem Van Kesteren, Eindhoven (NL); Josephus Arnoldus Henricus Maria Kahlman, Eindhoven (NL); Nicolaas Lambert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 256 days.

(21) Appl. No.: 14/380,852

(22) PCT Filed: Feb. 19, 2013

(86) PCT No.: PCT/IB2013/051325
§ 371 (c)(1),
(2) Date: Aug. 25, 2014

(87) PCT Pub. No.: WO2013/128329
PCT Pub. Date: Sep. 6, 2013

(65) Prior Publication Data
US 2015/0011852 A1 Jan. 8, 2015

Related U.S. Application Data

(60) Provisional application No. 61/605,253, filed on Mar. 1, 2012.

(51) Int. Cl.
A61B 5/1455 (2006.01)
A61B 5/1491 (2006.01)
(Continued)

(52) U.S. Cl.
CPC ........ *A61B 5/14552* (2013.01); *A61B 5/1491* (2013.01); *A61B 5/14556* (2013.01);
(Continued)

(58) Field of Classification Search
CPC ... A61B 5/0002; A61B 5/0059; A61B 5/1455; A61B 5/14551; A61B 5/14552; A61B 5/14532
USPC ....... 600/309, 310, 311, 312, 322, 323, 326, 600/329, 333, 340
See application file for complete search history.

(56) References Cited

U.S. PATENT DOCUMENTS 4,041,932 A * 8/1977 Fostick .............. A61B 5/14552
600/326
4,274,418 A 6/1981 Vesterager
(Continued)

FOREIGN PATENT DOCUMENTS

EP 0008460 A2 3/1980
RU 2336859 C2 10/2008
(Continued)

*Primary Examiner* — Eric Winakur
*Assistant Examiner* — Chu Chuan (JJ) Liu (57) ABSTRACT

An optical sensor unit (10) for measuring a concentration of a gas is provided, comprising at least one sensing layer (122) adapted to be irradiated with a predetermined radiation; at least one gas-permeable layer (121) adjacent to one side of the at least one sensing layer (122) and adapted to pass gas which concentration is to be measured through the gas-permeable layer (121) towards the sensing layer (122); a removable protective layer (150) covering at least the gas-permeable layer (121) and adapted to be removed before use of the optical sensor unit (10), wherein the optical sensor unit (10) is adapted to measure an optical response of the at least one sensing layer (122), which optical response depends on the concentration of the gas.

19 Claims, 7 Drawing Sheets

(51) Int. Cl.
*A61M 16/00* (2006.01)
*A61B 5/00* (2006.01)
*G01N 21/17* (2006.01)

(52) U.S. Cl.
CPC ....... *A61B 5/6833* (2013.01); *A61M 16/0069* (2014.02); *G01N 21/17* (2013.01); *A61M 2230/005* (2013.01); *A61M 2230/202* (2013.01); *A61M 2230/205* (2013.01)

(56) References Cited

U.S. PATENT DOCUMENTS

| | | | |
|---|---|---|---|
| 6,345,191 B1 | 2/2002 | Hartmann | |
| 6,503,198 B1* | 1/2003 | Aronowtiz | A61B 5/14532 600/309 |
| 6,602,716 B1 | 8/2003 | Klimant | |
| 7,443,302 B2* | 10/2008 | Reeder | A61B 5/0002 128/903 |
| 8,694,069 B1* | 4/2014 | Kosa | A61B 5/1455 600/342 |
| 2001/0034479 A1 | 10/2001 | Ring | |
| 2003/0050543 A1 | 3/2003 | Hartmann | |
| 2006/0004271 A1 | 1/2006 | Peyser | |

FOREIGN PATENT DOCUMENTS

| | | |
|---|---|---|
| WO | WO0182792 A1 | 11/2001 |
| WO | WO02056023 A1 | 7/2002 |
| WO | WO2013064313 A1 | 5/2013 |

* cited by examiner

SENSOR FOR DETERMINING CONCENTRATION OF GAS

CROSS-REFERENCE TO RELATED APPLICATIONS

This patent application claims the priority benefit under 35 U.S.C. §371 of international patent application no. PCT/IB2013/051325, filed Feb. 19, 2013, which claims the priority benefit under 35 U.S.C. §119 (e) of U.S. Provisional Application No. 61/605,253 filed on Mar. 1, 2012, the contents of which are herein incorporated by reference.

TECHNICAL FIELD OF THE INVENTION

The present invention relates to a sensor for determining concentrations of gases and a system comprising such a sensor.

BACKGROUND OF THE INVENTION

Neuromuscular disease, COPD and obese hypoventilation patients often suffer from chronic respiratory failure. Patients with chronic respiratory failure need regular treatment of their respiratory failure at home. Hypoxemic patients are treated by oxygen therapy while treatment by Non Invasive Ventilation (NIV) helps bringing the high carbon dioxide blood gas level of hypercapnic patients back to an acceptable level. The efficacy of the ventilation is checked by measuring the base-line and the trends in the arterial oxygen and carbon dioxide levels during NIV.

Arterial blood gas measurements form the golden standard. Before starting NIV at home, patients stay at the hospital to optimize ventilator settings and monitor arterial blood gas values. Depending on disease severity and stability, patients have to return more or less regularly to the hospital for checks. A respiratory nurse can also visit the patient at home to check the ventilator and to install equipment that enables non-invasive monitoring of blood gas partial pressures. At home, levels are monitored typically during a night and data are stored together with ventilator and respiratory data for later analysis at the hospital.

The state of the art in non-invasive blood oxygenation monitoring is by measuring the arterial oxygen saturation, which relates to the partial oxygen pressure via the oxygen dissociation curve. Pulse oximetry ($SpO_2$) is an optical method for non-invasive monitoring of arterial oxygen saturation in a patient and has become one of the most commonly used technologies in clinical practice. Pulse oximetry is a reasonably low cost technology and is easy to use. It is the preferred method for blood oxygenation monitoring at home.

The state of the art in non-invasive monitoring of the partial pressure of $CO_2$ is by means of capnography or by transcutaneous $CO_2$ ($PtcCO_2$) monitoring. For intubated patients with a healthy lung system the end tidal $CO_2$ ($etCO_2$) value obtained by capnography offers a good indication of the arterial $CO_2$ value. However, in case of non-invasive ventilation where air leaks between mask and face are usually present and the patients have severe respiratory diseases capnography is often not a reliable method. Moisture and dirt in the tubes connecting the patient's airway to ventilator can also influence the proper operation of a capnography sensor. In most hospitals a combination is used of capnography for trend monitoring and analysis of an arterial blood sample to obtain an occasional accurate value. Transcutaneous $CO_2$ monitoring is not disrupted by air-leaks, respiratory diseases and moisture but requires trained personal to obtain reliable values and shows some inaccuracy due to variation in skin properties among adults. At home $CO_2$ blood gas monitoring is less frequently used than oximetry despite its high relevance for patients receiving NIV.

The current transcutaneous $CO_2$ sensor generally comprises a thermostatically controlled heater to increase blood perfusion and gas-permeability of the skin and to stabilize the response of the sensor, a fluid layer between skin and sensor membrane, gas-permeable membrane covering the sensor, an electrolyte solution between membrane and sensor, a sensor comprising an electrochemical pH sensor and reference electrode, and an algorithm to compensate for temperature effects and skin metabolism.

The sensor membrane and electrolyte solution have to be replaced typically every 2 weeks or before use when the sensor has been unused for a long time. This requires some expertise because a fixed amount of electrolyte solution needs to be applied to the sensor and no air bubbles may be present in the solution. A special tool is required to fix the membrane gas-tight on top of the sensor and electrolyte solution. Due to drift of the sensor, the sensor needs to be calibrated every 4 to 8 hours using a gas mixture from a reference gas cylinder. Before application of the sensor to the skin, a fixed amount of contact fluid has to be applied into a fixation ring that has been attached to the skin.

US2001/0034479 describes an optically based transcutaneous blood gas sensor having a reusable sensor head and a disposable sensing cap. The reusable sensor has to be placed on the disposable sensing cap and thereafter this unit has to be placed in a disposable receptacle that is attached to the patient's skin by means of an adhesive film.

WO 02/056023 A1 discloses an optical sensor for determining at least one parameter in a sample. The optical sensor comprises an indicator material responding to the parameter and having a short luminescence decay time and a reference material not responding to the parameter and having a long luminescence decay time. The optical sensor detects the measuring signal indicating the parameter to be detected on the basis of the luminescence responses of the indicator and the reference material that are commonly detected. The indicator and the reference material are immobilized on a common support. The layer facing the sample of the indicator material and of the reference material is covered by a layer that allows contact between the indicator material and the sample but is substantially impermeable to the light used for exciting the indicator and the reference material.

SUMMARY OF THE INVENTION

It is an object of the present invention to provide a sensor for measuring a concentration of gas that can be employed easily and has low production costs, and which does not require tedious calibration before use. Further, a system and a method employing said sensor are provided.

This object is solved by the features of the independent claims.

The invention is based on the idea to combine into a single optical sensor unit at least one sensing layer and at least one gas permeable layer, and to cover at least the gas permeable layer with at least one removable protective layer being preferably gas-tight. Immediately before use, i.e. before the sensor unit is attached to an object releasing gas, for instance skin, the protective layer is removed. Hence, by covering at least the gas permeable layer with the at least one removable protective layer before usage the sensor unit keeps its known response to a gas to be measured. Hence, calibration can be handled during manufacturing and a calibration before use is not necessary.

According to one aspect of the present invention, an optical sensor unit for measuring a concentration of a gas comprises at least one sensing layer adapted to be radiated with a predetermined radiation, at least one gas permeable layer adjacent to one side of the at least one sensing layer and adapted to pass gas which concentration is to be measured through the gas permeable layer towards the sensing layer, and at least one removable protective layer covering at least the gas permeable layer and adapted to be removed before use of the optical sensor unit, wherein the optical sensor unit is adapted to measure an optical response of the at least one sensing layer which optical response depends on the concentration of the gas.

In an exemplary embodiment, when the optical sensor unit is attached to a person's skin, gasses present in the skin, for instance oxygen ($O_2$) or carbon dioxide ($CO_2$), pass the gas permeable layer which may be in direct contact with the skin and/or a contact medium that is arranged between the at least one gas permeable layer and the skin, into a sensing layer as long as the gas partial pressure in the skin is higher than the gas partial pressure in the sensor unit. Gas will pass the permeable membrane into or out of the sensing layer until equilibrium is established. The sensing layer, which is irradiated for instance with visible light, infrared light and/or ultraviolet light may generate luminescent light (optical response), the intensity as a function of time of which depends on the concentration of the gas being currently present in the sensing layer. From a measurement of that optical response (luminescent light in this example), a gas concentration in the skin can be derived.

Prior to attaching the optical sensor unit to the object of which the dissolved gas concentration needs to be determined (e.g. skin), the protective layer covering the gas permeable layer is removed. By providing the protective layer and removing the protective layer just before the sensor is attached to said object, no calibration of the sensor unit is necessary at this time. This is, since from manufacturing until use the gas permeable layer and preferably also the sensing layer are protected by the removable protective layer such that the gas permeable layer and the sensing layer keep the known response to the gas to be measured, for instance diffusion characteristics and optical response characteristics, respectively. Hence, calibration can be handled during manufacturing and a user has not to deal with a tedious calibration before use.

Preferably the optical sensor unit further comprises at least one optical transparent layer adjacent to the other or opposite side of the at least one sensing layer. The transparent layer (or transparent substrate) may cover the sensing layer and protect the same from direct contact with the surrounding atmosphere. Preferably, the at least one sensing layer is enclosed in particular by the gas permeable layer from one side and by the optical transparent layer from the other side. Because the gas permeable layer doesn't prevent moisture from entering and/or leaving the sensing layer a solution is provided according to this invention where the at least one sensing layer is packaged gastight during storage. The at least one optical transparent layer may be transparent only for selected wavelength ranges. For instance, when radiation in a first spectral range is used as the predetermined radiation for irradiating the sensing layer and radiation in a second spectral range is used to determine the response of the sensing layer, the at least one optical transparent layer may only allow the first and second spectral range of wavelengths to pass. This increases an accuracy and a sensitivity of the optical sensor unit.

Preferably the optical sensor unit further comprises a contact medium interposed at least between the at least one gas permeable layer and the at least one removable protective layer. The contact medium preferably comprises a gel or a liquid. The contact medium is preferably adapted to keep/control or influence a water content (moisture content) of the at least one gas permeable layer and/or the at least one sensing layer by establishing contact to a fluid with a fixed osmolality. In case the sensor unit is applied as a transcutaneous sensor the osmolarity is chosen at the value that corresponds to the osmolairy of the human skin. Hence, a shelf life of the optical sensor unit can be increased and a deterioration of optical response characteristics of the sensing layer and/or of diffusion characteristics of the gas-permeable layer can be prevented. Additionally or alternatively the contact medium is further adapted to guarantee fluid contact between the gas permeable layer and an object releasing gas. This further enhances an accuracy of the optical sensor unit. The contact medium preferably covers the gas-permeable layer entirely.

In a preferred embodiment, the optical sensor unit further comprises a second gas-permeable layer interposed between the contact medium and the removable protective layer. The gas-permeable layer preferably supports the contact medium and blocks unwanted substances transfer between the skin and sensing layer.

Preferably, a reservoir may be provided in the optical sensor unit to supply sufficient contact medium to the space between the protective layer and the at least one gas permeable layer.

Preferably, the optical sensor unit further comprises a structure adjacent to the at least one gas-permeable layer and having cavities and/or holes, wherein the contact medium is arranged in the cavities. The cavities and/or holes provide a kind of labyrinth keeping and supporting the contact medium.

Preferably the sensor unit further comprises an adhesive layer interposed between the at least one removable protective layer and a structure supporting at least the sensing layer and/or the gas permeable layer. The adhesive layer may have two functions. First, the adhesive layer may fix the removable protective layer to a structure supporting at least the sensing layer or the gas permeable layer, thus sealing the sensing layer and/or the gas permeable layer against direct contact with surrounding atmosphere (air or protective gas in a package). By this, a shelf life of the optical sensor unit can be increased and a deterioration of optical response characteristics of the sensing layer and/or of diffusion characteristics of the gas-permeable layer can be prevented. Second, the adhesive layer may be used to firmly fix the optical sensor unit to an object releasing or interchanging gas, for instance to skin, after the protective layer has been removed. Again, the adhesive layer that is in direct contact with the object releasing gas seals the gas permeable layer and/or the sensing layer from surrounding air, thereby preventing a deterioration of optical response characteristics of the sensing layer and/or of diffusion characteristics of the gas-permeable layer. The material for the adhesive could be the same as the material applied in adhesive bandage.

Preferably, the adhesive layer comprises a first adhesive layer, a second adhesive layer and a support layer interposed between the first adhesive layer and the second adhesive layer. The first adhesive layer may have an opening for exposing the at least one gas-permeable layer and/or the contact medium, wherein the second adhesive layer and the support layer cover said at least one gas-permeable layer and/or the contact medium. The second adhesive layer and the support layer may be at least partially perforated in a portion thereof corresponding to the gas-permeable layer. Thus, the first adhesive layer holds the support layer after removing the protective layer hold by the second adhesive layer.

Preferably, the at least one sensing layer comprises a luminescent material/luminophore. For monitoring oxygen the sensing layer may comprise fluorescent dye, and for monitoring $CO_2$ the sensing layer may comprise silicone rubber containing a pH responsive luminophore. The at least one sensing layer may be adapted to monitor oxygen and $CO_2$ simultaneously. Preferably, the sensing layer comprises first and second regions for detection oxygen and $CO_2$, respectively. This offers an extended application range of the optical sensor unit.

Preferably, the gas permeable layer is adapted to prevent light from passing through the gas-permeable layer. For instance, the gas permeable layer may be adapted to reflect or scatter light transmitted through the at least one sensing layer. Accordingly, an intensity of luminescent light measured by a detection device positioned adjacent to (i.e. above) the sensing layer or the optical transparent layer is increased, thereby increasing the signal-to-noise ratio and thus the sensitivity and accuracy of the optical sensor unit. The gas permeable layer being optically opaque also prevents light from the environment to influence the intensity of the light measured by the detection device from the sensing layer.

Preferably, the removable protective layer comprises plastic and/or metal and/or is optically opaque and/or is gas impermeable. Accordingly, a deterioration of characteristics of the gas-permeable layer and/or the sensing layer can prevented, which may be caused for instance by incident ambient light leading to photo bleaching of the luminescent dye in the sensing layer or evaporation of water from the sensing and/or gas permeable layer to surrounding atmosphere (e.g. air).

Preferably, the optical sensor unit further comprises at least one heating element and/or at least one temperature sensor. For instance, when the optical sensor unit is attached to a person's skin, the heating element may be adapted to increase blood perfusion and gas permeability of the skin, thereby increasing sensitivity and accuracy of the optical sensor unit and/or transcutaneous sensor unit. The heater could be in the form of a (zener) diode or may comprise a thin foil to minimize optical distances and thermal mass. Further, the heater is preferably a resistance heater or (zener) diode, so that the element can also be used as a temperature sensor, i.e. heater and temperature sensor are formed by the same element(s). This reduces costs and space required for installation of a heater and temperature sensor. However, the temperature sensor may also be realized as a separate element for sensing the temperature of the optical sensor unit to avoid injuries or burnings of the skin.

Preferably, the optical sensor unit is a transcutaneous sensor unit for measuring blood gas concentrations, in particular gas concentrations $O_2$ and/or $CO_2$. This application is advantageous, since it will enable to use a transcutaneous gas monitoring at home without expensive patient training or the presence of a trained nurse.

Preferably, the optical sensor unit comprises a first and a second sensing layer, wherein the first sensing layer is adapted to measure $O_2$ concentration and the second sensing layer is adapted to measure $CO_2$ concentration. The first and second sensing layer may be stacked, or may be arranged adjacent to each other with respect to a surface of an object releasing gas. This offers an extended application range of the optical sensor unit.

Preferably, the optical sensor unit further comprises at least one light source or light guiding structure adapted to irradiate the sensing layer with light, and at least one light guiding structure or detection advice adapted to detect the optical response of the sensing layer.

The at least one light source may be an active light source, such as a LED, and the at least one detection device may be a photosensitive device. Alternatively, a light guiding structure may be used to irradiate the sensing layer with the predetermined radiation. The light guiding structure may be arranged above the sensing layer/optically transparent layer and may be connected via an optical fiber to a light source external to the optical sensor unit. Light from the external light source is guided through the optical fiber and introduced into the light guiding structure, which is adapted to direct said light towards the at least one sensing layer. Further, the same light guiding structure may be used to collect the optical response of the sensing layer and to guide said optical response, for instance luminescent light, via the same or a different optical fiber to a device external to the optical sensor unit for analysis.

In a preferred embodiment a combination of both alternatives is employed. In particular, an active light source included in the optical sensor unit may be used to irradiate the sensing layer with the predetermined radiation, and a light guiding structure may be used to collect the optical response of the sensing layer and to guide said optical response, for instance luminescent light, via at least one optical fiber to a device external to the optical sensor unit for analysis. Preferably, the light is coupled into the sensing layer and luminescence light is collected through the same surface of the sensing layer. Alternatively, a light guiding structure connected via optical fibers to a light source external to the optical sensor unit may be used to direct light from an external light source and transmitted through at least one optical fiber towards the at least one sensing layer. At least one detection device, for instance a photosensitive device, may then be included to sense an optical response and may be adapted to generate e.g. electrical signals corresponding to the sensed optical response. Said signals may be transmitted to an external device for analysis. Alternatively, the optical sensor unit may be adapted to perform said analysis.

Preferably, the at least one light source and the at least one detection device form a unit detachably connected to a housing or structure of the optical sensor unit. Accordingly, the remaining parts of the optical sensor unit, for instance the sensing layer, gas permeable layer, removable protective layer, housing and/or supporting structure of the optical sensor unit may be disposable, wherein the remaining unit, that is the light source and the detection device, may be reused. This allows to save costs, since expensive parts such as light sources and/or detection devices and/or electronics are reused. By using light guiding structures it is possible to connect an input and/or output light guiding structure, which is/are coupled to the optical sensor unit. Thus, no additional unit needs to be connected to the optical sensor unit accommodating the light source and the at least one detection device.

According to another aspect of the present invention a system for patient monitoring and/or ventilation of a patient is provided, comprising an optical sensor unit as described above, a ventilation device and a monitoring device. The optical sensor unit may be operationally coupled to the monitoring device and/or to the ventilation device, wherein the monitoring device may be adapted to at least one of analyzing the optical response of the sensing layer, controlling the heating element and/or the temperature sensor, displaying the determined gas concentrations, and the like. Further, the monitoring device may function as an interface between the optical sensor unit and the ventilation device. Preferably, the monitoring device comprises means for calculating/determining the gas concentration from the measured/sensed optical response of the sensing layer, for instance from the sensed intensity or decay time of the luminescent light. When the sensing layer incorporates a gas-sensitive dye with a fast luminescence decay and a gas-insensitive reference dye with a slow luminescence decay a synchronous detection scheme can be applied. The intensity of the excitation light is modulated at a fixed frequency and the phase of the luminescence signal is detected and translated into a relative intensity of the gas sensitive dye from which the gas concentration can be determined. The means for calculating/determining the gas concentration may use an algorithm that is also adapted to compensate for temperature effects and skin metabolism. The monitoring device or ventilation device may include means for storing monitored data as a function of time. These data can be made available at a later time for analysis by a physician. Further, the ventilation device may be controlled on the basis of the measured/determined concentration of gas.

According to still another aspect of the present invention a method for measuring a concentration of gas is provided. The method uses an optical sensor unit comprising at least one sensing layer adapted to be irradiated with a predetermined radiation, at least one gas permeable layer adjacent to one side of the at least one sensing layer and adapted to pass gas which concentration is to be measured through the gas permeable layer towards the sensing layer, and a removable protective layer covering at least the gas permeable layer and adapted to be removed before use of the optical sensor unit, wherein the optical sensor unit is adapted to measure an optical response of the at least one sensing layer, which optical response depends on the concentration of the gas. The method preferably comprises the steps of removing the protective layer from the optical sensor unit, attaching the optical sensor unit to an object releasing gas, for instance to skin, receiving gas which concentration is to be measured in the sensing layer after passing the gas permeable layer, irradiating the sensing layer with the predetermined radiation, and sensing the optical response of the sensing layer, which depends on the concentration of the gas.

Even though the described embodiments will be explained in particular with reference to a transcutaneous non-invasive sensor for blood gas monitoring and a patient monitoring and/or ventilation device using the same, the inventive sensor may be readily applied to different spheres and other systems as well, such as other blood gas sensors, sensors for wound care and home health care products or in general to sensors for measuring gas concentrations.

DETAILED DESCRIPTION OF THE EMBODIMENTS

The optical sensor unit according to the present invention may be a ready-to-use sensor plaster for measuring blood gas concentrations. The ready-to-use sensor plaster combines into a single plaster unit a sensing spot that incorporates at least the sensing layer and a gas permeable layer (membrane). The plaster unit may further comprise an adhesive layer (film). The plaster unit is packaged in an air and light tight package in such a way that the unit keeps its known response to $CO_2$ and/or $O_2$. After opening the package and removal of the protective layer (protection foil) covering the sensing spot and adhesive layer, the plaster unit can be attached directly to a patient's skin. The ready-to-use sensor plaster may be typically used for monitoring during one night but can also be used for monitoring during a couple of days. After removal of the sensor from the skin the sensor plaster may be disposed. Calibration is handled during manufacturing. Calibration before use and separate application of a contact fluid between sensor and skin is not necessary. Due to the application of chemo-optical technology instead of electrochemical technology, application of an electrolyte solution will also not be required. The present invention uses one or more gas-permeable membranes to separate the sensing layer, for instance a luminescent dye, from the skin. These membranes will be applied during manufacturing as part of the sensor spot and do not need to be installed separately and calibrated before use.

Figure 1:
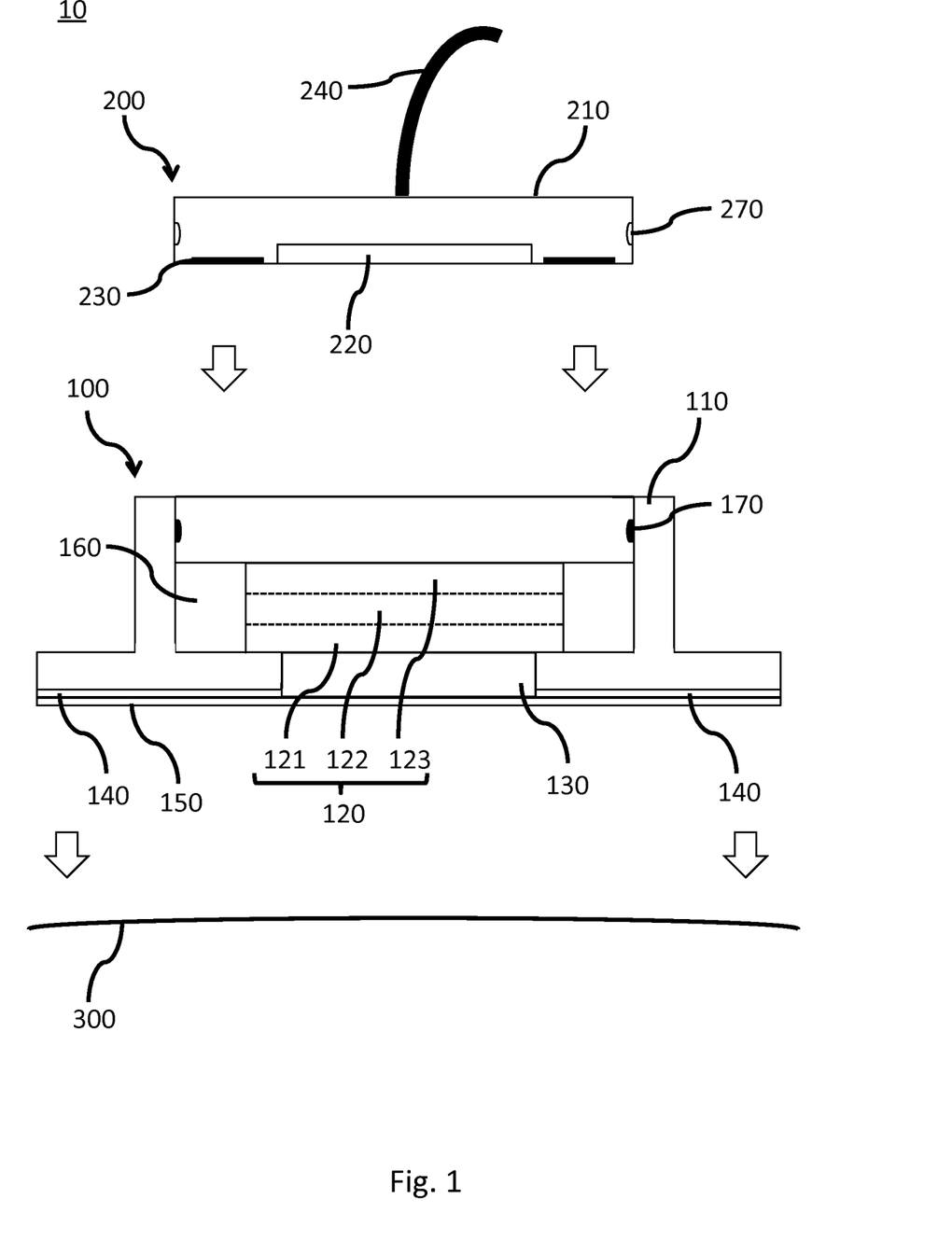
FIG. 1 shows a sectional view of an optical sensor unit according to a first embodiment of the present invention.

FIG. 1 shows a sectional view of an optical sensor unit 10 according to a first embodiment of the present invention. The optical sensor unit 10 may have a circular shape. The optical sensor unit 10 comprises a first device 100 and a second device 200. The second device 200 is preferably detachable from the first device 100. Preferably, the second device is reusable and the first device 100 is disposable. In use, the first device 100 may be attached to a patient's skin 300 and the second device 200 may be operatively coupled to the first device 100.

The first device 100 comprises a sensor spot 120 including at least one gas permeable layer 121, at least one sensing layer 122 and at least one optically transparent layer 123. The at least one sensing layer 122 is situated in between the gas permeable layer 121 and the optically transparent layer 123. The optically transparent layer being substantially gastight, in order to prevent a deterioration of the sensing/optical response characteristics of the sensing layer 122. The sensor spot 120 may be supported by supporting structure 110. The supporting structure 110 may be of a cylindrical shape and may comprise an upper opening and a lower opening. In the lower opening just below the sensor spot 120 there may be provided a contact medium 130, which may include a contact gel for keeping/controlling water content of the gas-permeable layer 121 and/or the sensing layer 122 as well as to guarantee a fluid contact between the gas permeable membrane 121 and the skin 300 during use.

A heating element 160 may be provided for instance at a lateral side of the sensor spot 120 for heating the skin 300 to increase blood perfusion and gas permeability of the skin 300. The heating element may have a cylindrical shape or any other suitable shape. The heating element 160 may be for instance a resistance heater that is supplied with power via contact element 230 of the second device. Alternatively, the heating element 160 of the first device 100 may include a heat conducting material that is heated by a (resistance) heater included in the contact element 230. In both embodiments the contact element 230 is in electrical and/or thermal contact with heating element 160. Instead of an electrical contact an inductive coupling can be applied. In that case contact element 230 comprises a first induction coil and heating element 160 a second induction coil. In first device 100 an electrical circuit is formed by the second induction coil and a dissipating element, e.g. a resistor, (zener-)diode or obviously the wire resistance of the coil itself. By applying a current into the first induction coil, a current is induced in the second coil which causes heat dissipation. A further advantage of the inductive coupling scheme is that no direct galvanic contact between heater electronics in device 200 and device 100 on the skin 300 is present. This eases the design—and lowers the costs—of the heater controller as electrical protective means may be omitted. Note that the temperature reading is not affected by the thermal contact resistance between device 100 and device 200 as long as device 200 is thermally well isolated from the environment and the thermal contact resistance between device 100 and 200 is significantly smaller than the thermal resistance of device 200 to the environment. This constraint can easily be met by adequate thermal isolation of the connector.

In FIG. 1 the heating element 160 heats the supporting structure 110, which in turn heats the underlying skin 300. However, in other embodiments the heating element 160 may contact the skin 300 directly. In such a case the supporting structure 110 may have an L-shape instead of the inverse T-shape shown in FIG. 1, and the heating element 160 may extend to the adhesive layer 140.

The lower side of the supporting structure 110 is covered by a removable protective layer 150. The removable protective layer 150 is provided to protect the sensor spot and/or the contact medium 130 from direct contact with surrounding atmosphere and/or from incident ambient light. The protective layer 150 is attached to the supporting structure 110 by means of the adhesive layer 140. The adhesive layer 140 may be provided with an opening such that the contact medium and/or the sensor spot are not covered by the adhesive layer. Hence, at least a portion of the contact medium 130 is direct contact with the skin 300.

During storage the substantially gas-tight transparent layer 123, the gas-tight heating element 160 or a gas-tight structure in-between the heating element and sensor spot and the protective layer 150 completely enclose the sensing layer 122, membrane layer 121 and contact medium 130 thereby preventing a deterioration of the characteristics of the optical sensor unit. Before use, the protective layer 150 is removed and the first device 100 is attached to the skin 300. The adhesive layer 140 may prevent a leakage of surrounding air to the contact medium 130 and/or the gas permeable membrane and/or the sensing layer, thereby preventing a deterioration of the characteristics of the optical sensor unit.

The second device 200 may comprise an optical device 220 comprising at least one light source and at least one detection device. The second device 200 is preferably of circular shape and adapted to fit into the upper opening of the supporting structure 110. Means for fixing the first device 100 and the second device 200 to each other may include a snap fit 170, 270 provided on lateral surfaces of an inner side wall defining the upper opening of the supporting structure 110 and a outer side wall of the second device 200, respectively.

The optical device 220 may be in direct contact with the optically transparent layer 123. The at least one light source of the optical device 220 may be an active light source, such as an LED, and the at least one detection device of the optical device 220 may be a photosensitive device. Preferably, a light guiding structure may be used to irradiate the sensing layer 122 with the predetermined radiation, preferably visible light, infrared light and/or ultraviolet light. The light guiding structure may be arranged above the sensor spot 120 and may be connected via optical fibers included in supply line 240 to a light source external to the optical sensor unit 10. Light from the external light source is guided through the optical fibers of the supply line 240 and introduced into the light guiding structure of the optical device 220, which is adapted to direct said light towards the at least one sensing layer 122. Further, the same light guiding structure of the optical device 220 may be used to collect the optical response of the sensing layer 122 and to guide said optical response, for instance luminescent light, via the same or different optical fibers included in the supply line 240 to a device external to the optical sensor unit 10 for analysis.

Alternatively, a combination of the above-described alternatives is used. In particular, an active light source such as an LED included in the of the optical device 220 may be used to irradiate the sensing layer 122, and a light guiding structure also included in the optical device 220 may be used to collect the optical response of the sensing layer 122 and to guide said optical response, for instance luminescent light, via at least one optical fiber in the supply line 240 to a device external to the optical sensor unit 10 for analysis. Alternatively, a light guiding structure of the optical device 220 connected via at least one optical fibers included in the supply line 240 to a light source external to the optical sensor unit 10 may be used to direct light from the external light source that is transmitted through the at least one optical fiber towards the at least one sensing layer 122. At least one detection device, for instance a photosensitive device, included in the optical device 220 is used to sense an optical response. Said detection device may be adapted to generate e.g. electrical signals corresponding to the sensed optical response. Said signals may then be transmitted to an external device for analysis. Alternatively, the optical sensor unit 10 may be adapted to perform said analysis and to output the analysis results to some external device.

Preferably, the first device 100 is disposable and the second device 200 is reusable. In particular, the passive device may not include any expensive electronics at all. Hence, the first device 100 can be manufactured with low effort and reduce costs, wherein the second device 200 including the electronics may be reused and may also for instance be used with different first devices 100 from measuring concentration of different gases (for instance $O_2$ and $CO_2$). This provides increased flexibility of the optical sensor unit 10.

During operation a temperature of the heating element 160 and preferably of the contact fluid 130 and sensing layer 122 may be increased by the heating element 160 to a temperature in the range of 42° to 45° Celsius to increase capillary blood flow in the skin and bring the capillary blood gas levels close to the arterial blood gas levels. During operation the sensor temperature may be measured by at least one temperature sensor included in the heating element 160 and/or the contact element 230 and/or by a separately provided temperature sensor. The temperature may be controlled such as to have a well defined measurement condition and to prevent burning the skin 300.

In a preferred embodiment, through the fiber included in the supply line 240 and the light guiding structure included in the optical device 220, the sensing spot 120 is illuminated and the luminescence is collected and transported to a monitoring device 20 including an optoelectronic circuit for detection and signal analysis. After signal detection and compensation for temperature dependent effects in sensor unit and skin 300 the derived gas concentration level may be transferred to another external device for data display and storage, for instance to a ventilating device 30 connected to the optical sensor unit 10 via the monitoring device 20 (for details see FIG. 4).

It is preferred that all sensor spots from a manufacturer show the same response as a function of gas concentration level. The response upon gas concentration is described by a number of constants and these constants are set as fixed parameters in an external device (e.g. the monitoring device 20) to translate the signal of the optical sensor unit 10 into gas concentration values that can be displayed on a display means or stored on for instance a SD-card for later analysis by a physician.

Batch wise calibration can provide an alternative when the manufacturing cannot be controlled to such an extent that sensor spots 120 from different batches show the same response. In that case the constants describing the response will be determined by the manufacturer for one or a few sensor spots 120 from a certain batch and supplied with all the sensor spots 120 from the batch. The care provider taking care of distribution of the transcutaneous plasters to the patients can provide a specific patient simultaneously with a plaster and a SD-card for data storage, wherein the latter includes the constants describing the sensor response. Upon connection of the transcutaneous sensor to an external device 20, 30 and insertion of the SD-card in said external device 20, 30 for data storage, the external device 20, 30 reads the constants from the SD-card and performs an accurate translation of sensor spot signals to gas concentration levels without involvement of the patient and/or a nurse and/or a physician.

Figure 2:
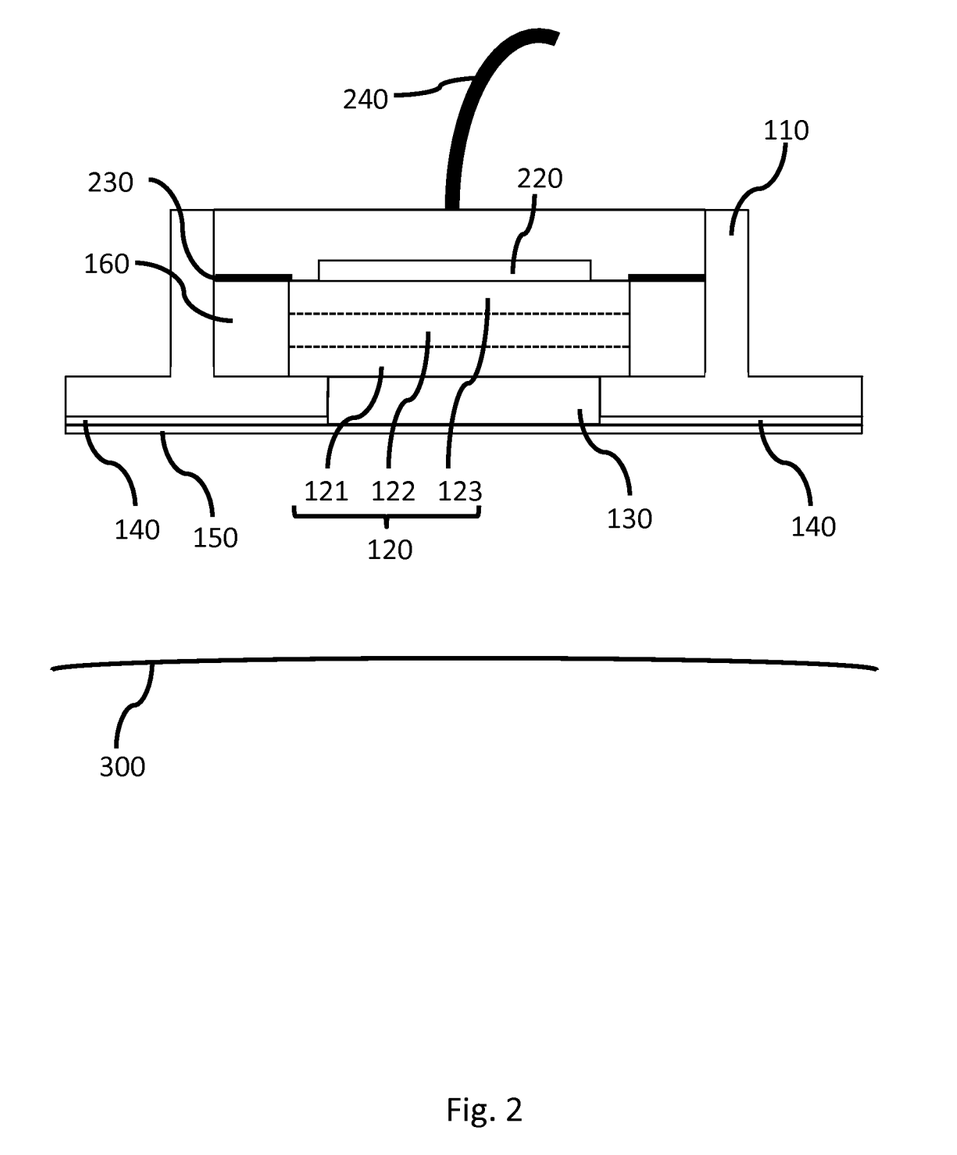
FIG. 2 shows a sectional view of an optical sensor unit according to a second embodiment of the present invention.

FIG. 2 shows a sectional view of an optical sensor unit 10 according to a second embodiment of the present invention. The embodiment shown in FIG. 2 differs from the embodiment shown in FIG. 1 in that the second device 200 is formed integrally with the first device 100. In this embodiment the optical sensor unit 10 may be reusable or disposable as a whole.

Figure 3:
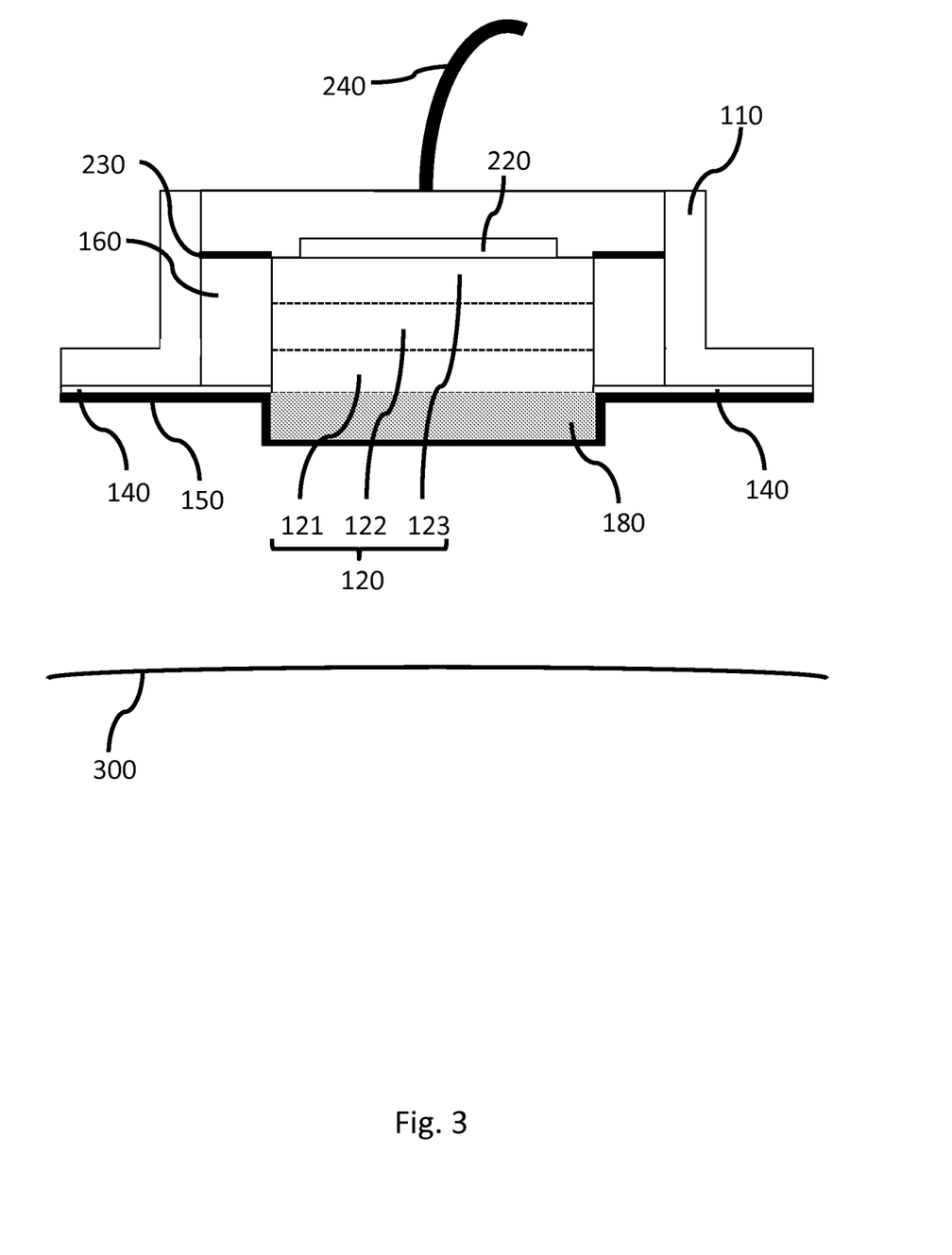
FIG. 3 shows a sectional view of an optical sensor unit according to a third embodiment of the present invention.

FIG. 3 shows a sectional view of an optical sensor unit 10 according to a third embodiment of the present invention. The embodiment shown in FIG. 3 differs from the embodiments shown in FIGS. 1 and 2 in that no contact medium 130 is provided. Instead, below the gas permeable layer 121 a reservoir with a liquid 180, for instance a buffer solution, 180 is provided. Accordingly, after removal of the protective layer 150, the buffer solution 180 is dismissed and the gas permeable layer 121 can be brought into direct contact with the skin 300 of a patient. The gas permeable layer 121 may be a flexible silicone rubber membrane with a high moisture content that provides good contact to the skin during transcutaneous measurements. The buffer solution 180 is preferably adapted to keep/control a water content (moisture content) of the at least one gas permeable layer and/or the at least one sensing layer. Hence, a shelf life of the optical sensor unit can be increased and a deterioration of optical response characteristics of the sensing layer and/or of diffusion characteristics of the gas-permeable layer can be prevented.

The protective layer 150 may be shaped such that a reservoir, i.e. a space that can accommodate the buffer solution 180, is provided below the sensor spot 120.

A further difference to the embodiments shown in FIGS. 1 and 2 is that in FIG. 3 the heating element 160 is in direct contact with the adhesive layer 140. However, the embodiments shown in FIGS. 1, 2 and 3 could be combined, i.e. the embodiment shown in FIG. 3 could include the contact medium 130 and/or the heating element 160 shown in FIGS. 1 and 2. Further, the second device 200 shown in FIG. 3 could be detachable from or integrally formed with the first device 100, as shown in FIGS. 1 and 2, respectively. Further, the configuration of the optical device 220 described with respect to FIG. 1 could be the same or essentially the same for the embodiments of FIGS. 2 and 3.

Figure 4:
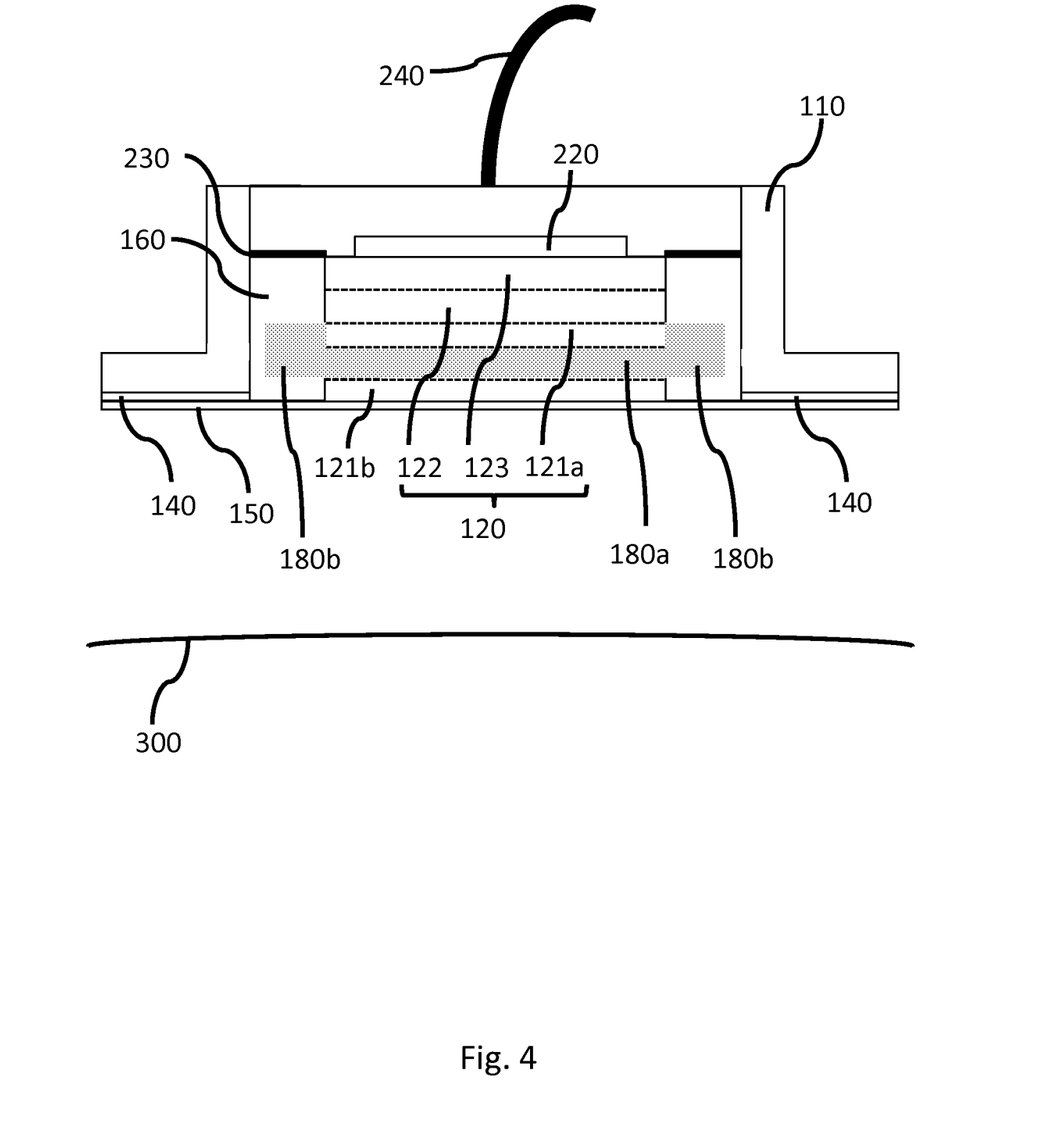
FIG. 4 shows a sectional view of an optical sensor unit according to a fourth embodiment of the present invention.

FIG. 4 shows a sectional view of an optical sensor unit 10 according to a fourth embodiment of the present invention. The optical sensor unit 10 according to a fourth embodiment is similar to the third embodiment shown in FIG. 3. In particular, the optical sensor unit 10 shown in FIG. 4 also includes a liquid or fluid 180 but two gas-permeable membranes, i.e. a first and a second gas-permeable membrane 121*a* and 121*b*.

The first and the second gas-permeable membrane 121*a* and 121*b* are arranged as to confine a thin fluid layer 180*a* there between. The fluid film 180*a* is preferably located below the sensor spot 120 and connects to a reservoir 180*b* situated in the area around the sensor spot 120 or elsewhere in the sensor unit 10. The heating element 160 may comprise at least one compartment for providing said reservoir 180*b*. The osmolarity of the fluid 180 controls the water content of the gas-permeable membranes 121*a*, 121*b* and the sensing layer 122 during storage. During operation it provides a buffer to changes in humidity and osmolarity on the skin. Additionally, the second membrane 121*b* blocks unwanted substances transfer between sensor spot 120 (121*a*, 122,123) and skin 300.

The composition of the two membranes 121*a*, 121*b* can be different to obtain a higher selectivity towards wanted and unwanted transfer of substances towards the sensing layer 122. The thickness of the fluid film 180*a* in between the gas-permeable membranes 121*a*, 121*b* should be sufficiently thin to limit its effect on the response time of the sensor unit 10. Preferably, its thickness is typically less than one millimeter and more preferably in the range of one tenth of a millimeter. A spacer structure in between the membranes may further be provided to control the thickness of the fluid film 180*a*.

Figure 5:
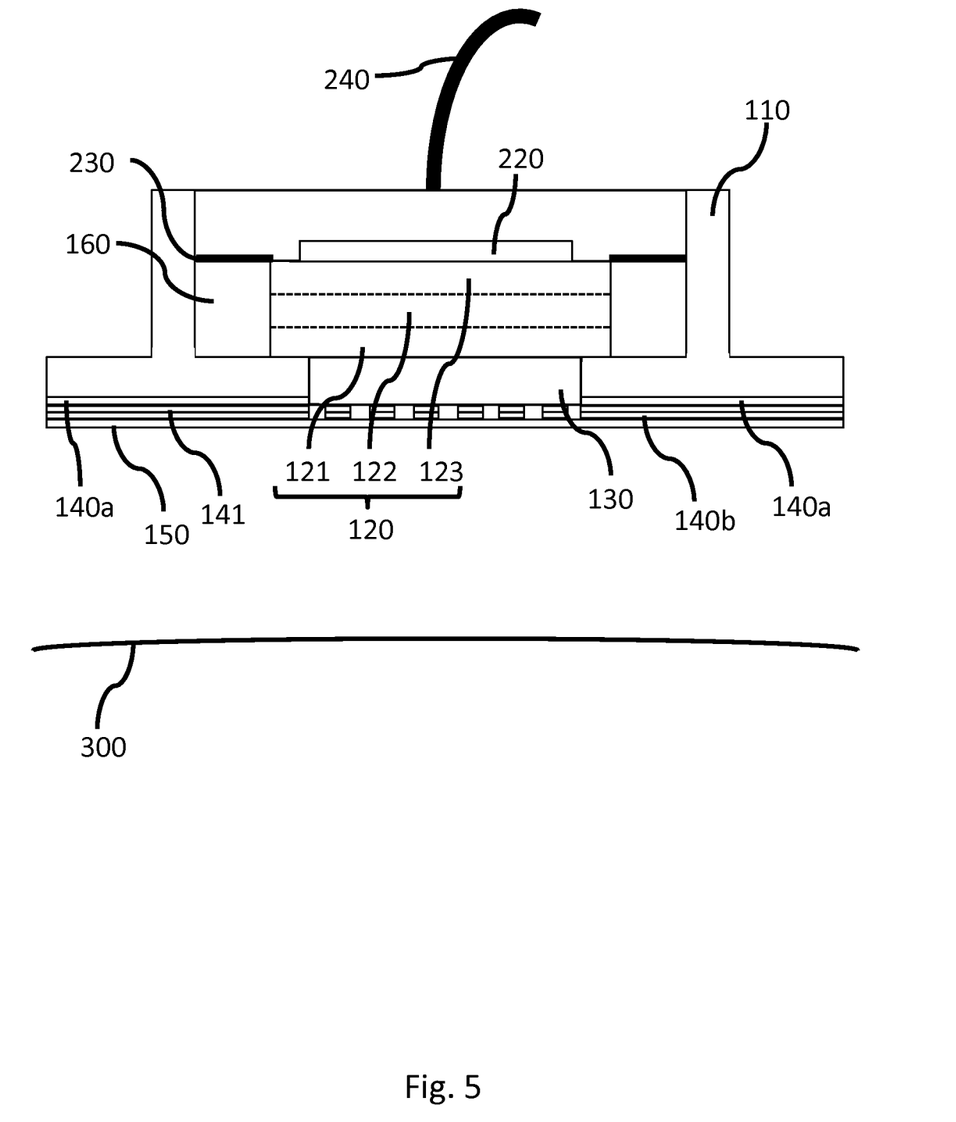
FIG. 5 shows a sectional view of an optical sensor unit according to a fifth embodiment of the present invention.

FIG. 5 shows a sectional view of an optical sensor unit 10 according to a fifth embodiment of the present invention. The optical sensor unit 10 according to a fifth embodiment is similar to the second embodiment shown in FIG. 2. In particular, the optical sensor unit 10 shown in FIG. 5 also includes a contact medium 130 but two adhesive layers, i.e. a first and a second adhesive layer 140*a*, 140*b*, and a support layer 141 disposed there between.

The first adhesive layer 140*a* substantially corresponds in shape and characteristics to the adhesive layer 140 shown in FIGS. 1-4. The second adhesive layer 140*b* and the support layer 141 are used to fix the location of the contact medium 130, and the second adhesive layer 140*b* is further used to glue the sensor unit 10 to the skin 300 (in analogy to the adhesive layer 140 of the first to fourth embodiments). At the location of the contact medium 130, the second adhesive layer 140b and the support layer 141 may be perforated to enable gas transport between sensor unit 10 and skin 300. The second adhesive layer 140b may be formed by a thin double-sided adhesive tape covering the total plaster surface.

Figure 6:
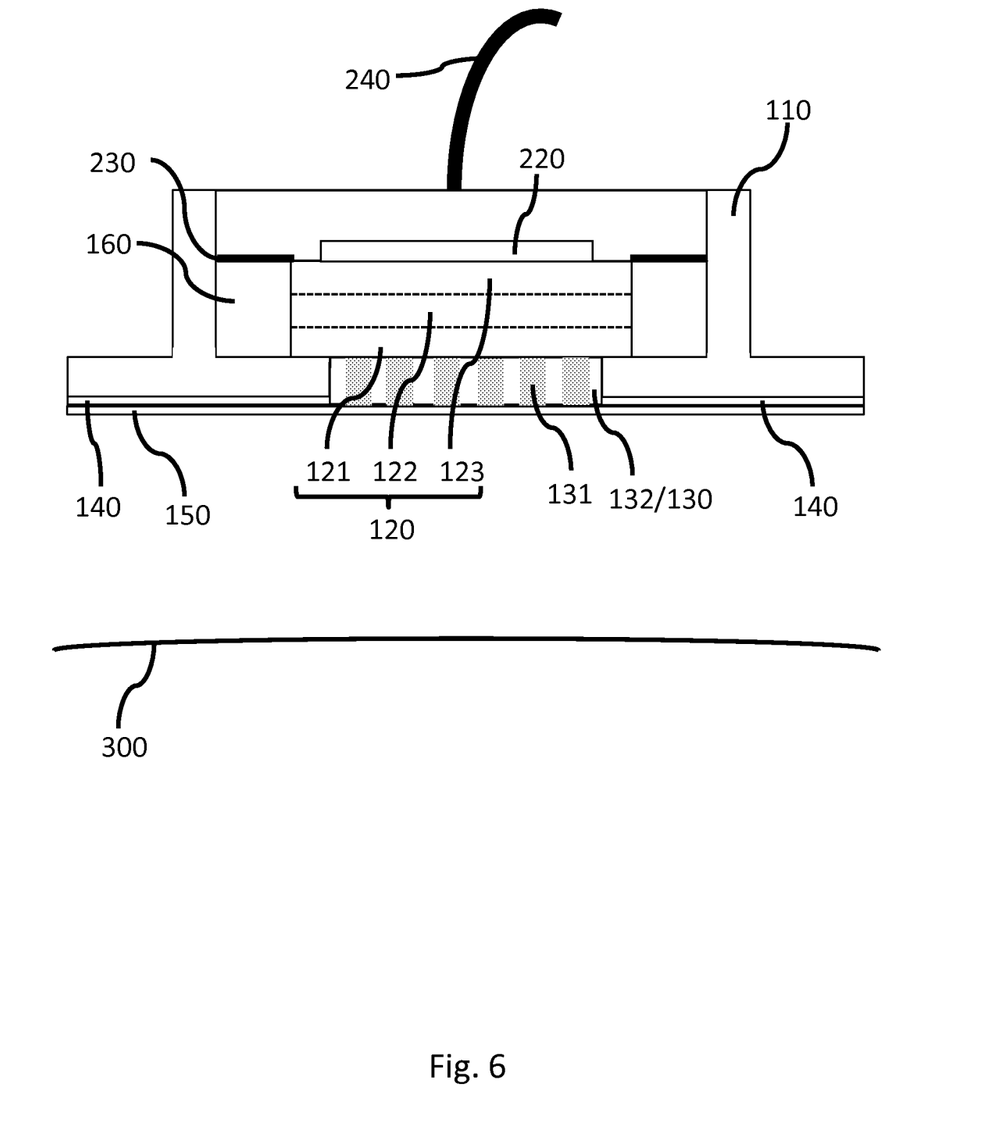
FIG. 6 shows a sectional view of an optical sensor unit according to a sixth embodiment of the present invention.

FIG. 6 shows a sectional view of an optical sensor unit 10 according to a sixth embodiment of the present invention. The optical sensor unit 10 according to a sixth embodiment is similar to the second embodiment shown in FIG. 2. In particular, the optical sensor unit 10 shown in FIG. 6 also includes the contact medium 130 and a structure 131 located below the sensor spot 120.

Preferably, the structure 131 is located on top of the gas-permeable membrane 121. The structure 131 is adapted to fix the position of the contact medium 130 after repelling the removable foil. The structure 131 may comprise at least one cavity 132 for accommodating the contact medium 130. Preferably, the cavities 132 define a labyrinth-structure of the structure 131. Further, a thickness of the contact medium 130 may be substantially equal to or greater than a thickness of the structure 131. Preferably, the contact medium 130 contacts the gas-permeable layer 121 and/or the skin 300 after attaching the sensor unit 10 thereto. Alternatively the structure 121 may be provided between the sensor spot 120 and the contact medium 130.

The contact medium 130 may be a geld or liquid/fluid (e.g. a buffer solution).

Further, the structure 131 could also be applied to the fourth embodiment shown in FIG. 4 in the reservoir 180b and/or in the space provided for the fluid layer 180a, e.g. to fix the location of the first and second membrane 121a, 121b with respect to each other.

The second device 200 shown in FIGS. 4-6 could be detachable from or integrally formed with the first device 100, as shown in FIGS. 1 and 2, respectively. Further, the configuration of the optical device 220 described with respect to FIG. 1 could be the same or essentially the same for the embodiments of FIGS. 4-6. Furthermore, in the fifth and sixth embodiment the structure of the heating element 160 could be essentially the same as it is shown for the third embodiment, i.e. the heating element 160 could extend to the adhesive layer 140.

Alternatively, it is possible in all embodiments to use additionally or alternatively a rubber sealing and a belt instead of the adhesive layer for attaching the optical sensor unit to the skin. When removing the protective layer 150 the adhesive layer 140 is removed and the rubber sealing preferably surrounding the lower opening of the supporting structure 110 is exposed and could be placed on the skin of the patient. However, it is also possible to use the adhesive layer and the rubber sealing for fixing the optical sensor unit and for sealing the place of measurement. For fixing such kind of optical sensor unit a belt or hook-and-loop fastener may be used.

Figure 7:
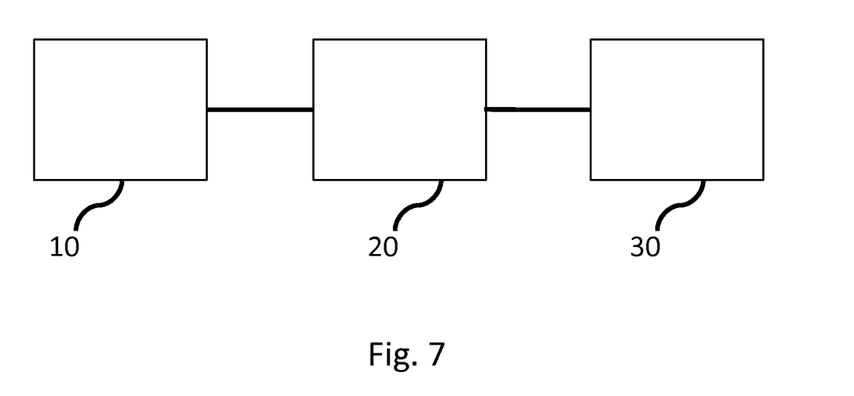
FIG. 7 shows a system including an optical sensor unit according to the present invention.

FIG. 7 shows a system for patient monitoring and/or ventilation of a patient, comprising an optical sensor unit 10 according to the present invention, a ventilation device 30 and a monitoring device 20. The monitoring device 20 may function as an interface between the optical sensor unit 10 and the ventilation device 30. The monitoring device 20 may include optoelectronics for supplying the optical sensor unit 10 with light via optical fibers included in supply line 240 and optical device 220, and for receiving luminescent light from the sensing layer 121 via optical device 220 and optical fibers included in supply line 240. The monitoring device 20 may further comprise means for determining/calculating a gas concentration based on the received optical response, for instance light intensity of the luminescent light generated in the sensing layer 123. The monitoring device 20 may further comprise a heater controller for controlling the temperature of the heating element 160. The heater controller may be adapted for detecting the temperature of the heating element 160 using the temperature sensor included in the optical sensor unit 10 and for adjusting for instance a current flowing through a resistance heater included in the heating element 160 or the contact element 230 based on the detected temperature. The monitoring device 20 may further comprise means for communication with the ventilation device 30. Said communication means may include at least one communication technique, such as wired (cable), wireless (Bluetooth, infrared, RF), and the like.

The ventilation device 30 may include all functions associated with the state of the art ventilation device for invasive or non-invasive ventilation of a patient with respiratory failure, and may further comprise display means and storage device for displaying and storing information/data received from the monitoring device 20. In particular, the display means of the ventilation device 30 may be adapted to display a gas concentration determined by the monitoring device 20 and may further store gas concentration information over a predetermined time period for instance for later evaluation by a physician or for close loop adaptation of the ventilation settings. The monitoring device may be a stand-alone device or a device clicked onto the ventilator or be included in the ventilation device 30.

Figure 8:
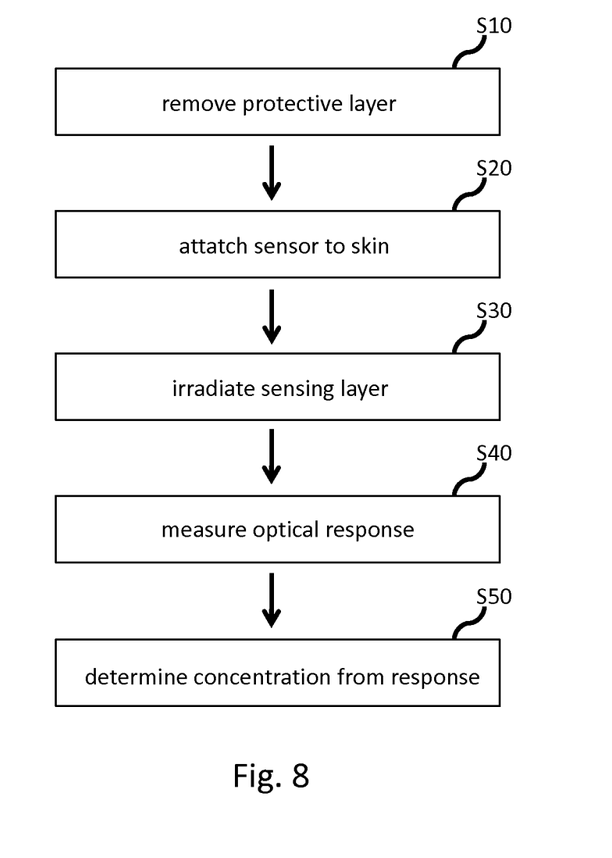
FIG. 8 shows a flow diagram of a method for measuring a concentration of gas using an optical sensor unit according to the present invention.

FIG. 8 shows a flow diagram of a method for measuring a concentration of gas using an optical sensor unit 10 according to the present invention. In step S10, the protective layer 150 is removed from the optical sensor unit 10. Then, in step S20, the optical sensor unit 10 is attached to the skin 300 of a patient. The contact medium 130 or the gas permeable layer 121 contacts the skin. The adhesive layer 150 that is firmly attached to the skin and preferably seals the contact areas (sensor spot 120) from surrounding air. After attaching the optical sensor unit 10, the heating element 160 may be used to heat the skin 300 underlying the optical sensor unit 10 in order to increase capillary blood flow in the skin and bring the capillary blood gas levels close to the arterial blood gas levels. Gas, which leaves the skin and which concentration is to be measured, passes the gas permeable layer 121 providing a predetermined diffusion rate and reaches the sensing layer 122. In step S30, the sensing layer 122 is irradiated with predetermined radiation, which is preferably visible light, infrared or UV-radiation. Irradiating the sensing layer 122 causes the sensing layer to generate luminescent light, the intensity of which depends on the concentration of the gas diffused into the sensing layer 122. In particular, the intensity of the luminescent light varies according to the concentration of the gas in the sensing layer 122. In step S40, the optical response, i.e. an intensity of the luminescent light is measured/sensed by optical device 220. Preferably, the luminescent light is guided via optical device 220 and optical fibers in supply line 240 to the monitoring device 20, which monitoring device 20 is adapted to determine/calculate a concentration of gas in step S50 from the optical response and in particular based on the intensity of the sensed fluorescent light. The monitoring device 20 may then transmit the determined gas concentration to the ventilation system 30 for displaying and storage.

It is an advantage of the present invention that a calibration of the optical sensor unit is handled during manufacturing, and a calibration before use and a separate application of a contact fluid between the sensor and skin are not necessary. Due to the application of chemo-optical technology instead of conventional electrochemical technology application electrolyte solution is also not required. According to the invention, a gas permeable membrane and preferably a contact medium are used to separate the sensing layer (e.g. comprising a luminescent dye) from the object releasing gas (e.g. skin). These elements are applied during manufacturing as part of the sensor spot and do not need to be installed separately before use.

The invention claimed is:

1. Optical sensor unit for measuring a concentration of a gas, comprising:
   a first gas-permeable layer adjacent to a first side of at least one sensing layer and adapted to pass gas which concentration is to be measured through the first gas-permeable layer towards the at least one sensing layer;
   the at least one sensing layer adapted to be irradiated with a predetermined radiation and to emit a corresponding optical response, wherein the optical response depends on the concentration of the gas;
   a fluid film or a contact medium interposed between the first gas-permeable layer and a second gas-permeable layer, the fluid film or the contact medium being on a side of the first gas-permeable layer that is opposite the at least one sensing layer,
   a removable protective layer covering at least the second gas-permeable layer and adapted to be removed before use of the optical sensor unit; an adhesive layer interposed between the removable protective layer and a structure supporting at least the at least one sensing layer and/or the first gas-permeable layer; and
   the second gas-permeable layer interposed between the removable protective layer and the fluid film or the contact medium, wherein the first gas-permeable layer and the second gas-permeable layer confine at least part of the fluid film or the contact medium there-between.

2. Optical sensor unit of claim 1, wherein it is the contact medium that is interposed between the first gas-permeable layer and the second gas-permeable layer, the contact medium being a gel or a liquid, wherein the contact medium is adapted to control the water content of the first gas-permeable layer and/or the at least one sensing layer.

3. Optical sensor unit according to claim 1, further comprising an optically transparent layer adjacent to a second side of the at least one sensing layer and adapted to cover and protect the at least one sensing layer from direct contact with a surrounding atmosphere.

4. Optical sensor unit according to claim 1, further comprising a structure adjacent to the first gas-permeable layer and having cavities, wherein it is the contact medium that is interposed between the first gas-permeable layer and the second gas-permeable layer, and wherein the contact medium is arranged in the cavities.

5. Optical sensor unit according to claim 1, wherein the adhesive layer is attached to an object interchanging gas after removal of the protective layer.

6. Optical sensor unit according to claim 1, wherein the adhesive layer comprises a first adhesive layer, a second adhesive layer and a support layer interposed between the first adhesive layer and the second adhesive layer.

7. Optical sensor unit according to claim 6,
   wherein it is the contact medium that is interposed between the first gas-permeable layer and the second gas-permeable layer, and
   wherein the first adhesive layer has at least one opening for exposing the first gas-permeable layer and/or the contact medium, the second adhesive layer and the support layer covering the first gas-permeable layer and/or the contact medium and being perforated in a portion thereof corresponding to the first gas-permeable layer.

8. Optical sensor unit according to claim 1, wherein the at least one sensing layer comprises a luminescent material.

9. Optical sensor unit according to claim 1, wherein the first gas-permeable layer is adapted to prevent light from passing through the first gas-permeable layer.

10. Optical sensor unit according to claim 1, wherein the removable protective layer comprises plastic and/or metal and/or is optically opaque and/or is gas-impermeable.

11. Optical sensor unit according to claim 1, wherein the optical sensor unit is a transcutaneous sensor unit for measuring blood gas concentrations, in particular gas concentrations of $O_2$ and/or $CO_2$.

12. Optical sensor unit according to claim 1, further comprising:
    at least one light source or at least one light guiding structure adapted to irradiate the sensing layer with light;
    the at least one light guiding structure or a detection device adapted to detect the optical response of the sensing layer, wherein at least one of the light source, light guiding structure and/or the detection device are detachably connected to the optical sensor unit.

13. System for patient monitoring and/or ventilation of a patient, comprising an optical sensor unit according to claim 1, a ventilation device and a monitoring device.

14. Optical sensor unit according to claim 1, further comprising:
    a heating element provided at a lateral side of the at least one sensing layer and the first gas-permeable layer for heating skin of a patient to increase blood perfusion and gas permeability of the skin.

15. Optical sensor unit according to claim 14, wherein the heating element comprises a compartment for providing a reservoir that connects to the fluid film or the contact medium.

16. Optical sensor unit according to claim 1, wherein one or more of the at least one sensing layer, the first gas-permeable layer, and the removable protective layer are packaged in an air and light tight package during storage.

17. A method for measuring a concentration of gas using an optical sensor unit comprising a first gas-permeable layer adjacent to one side of at least one sensing layer and adapted to pass gas which concentration is to be measured through the first gas-permeable layer towards the at least one sensing layer, the at least one sensing layer adapted to be irradiated with a predetermined radiation and to emit a corresponding optical response, the optical response depending on the concentration of the gas, a fluid film or a contact medium interposed and confined between a side of the first gas-permeable layer that is opposite the at least one sensing layer and a second gas-permeable layer, the fluid film or the contact medium being a gel, fluid, buffer solution, or a liquid, the second gas-permeable layer interposed between a removable protective layer and the fluid film or the contact medium, an adhesive layer interposed between the removable protective layer and a structure supporting at least the at least one sensing layer and/or the first gas-permeable layer, and the removable protective layer covering at least the second gas-permeable layer and adapted to be removed before use of the optical sensor unit, wherein the fluid film or the contact medium is adapted to control the water content of the first gas-permeable layer and/or the at least one sensing layer, the method comprising the steps of:
- removing the protective layer from the optical sensor unit,
- attaching the optical sensor unit to an object releasing gas using the adhesive layer,
- receiving gas which concentration is to be measured in the at least one sensing layer after passing the first gas-permeable layer,
- irradiating the at least one sensing layer with the predetermined radiation, and
- sensing the optical response of the at least one sensing layer, which depends on the concentration of the gas.

18. The method according to claim 17, wherein the optical sensor unit further comprises a heating element provided at a lateral side of the at least one sensing layer and the first gas-permeable layer for heating skin of a patient to increase blood perfusion and gas permeability of the skin.

19. The method according to claim 18, wherein the heating element comprises a compartment for providing a reservoir that connects to the fluid film or the contact medium.

* * * * *